United States Patent
Takei et al.

(10) Patent No.: US 6,394,991 B1
(45) Date of Patent: May 28, 2002

(54) ABSORBENT ARTICLE

(75) Inventors: Shinobu Takei; Kazuhiro Tagawa, both of Tochigi-ken (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/629,168

(22) Filed: Jul. 31, 2000

(30) Foreign Application Priority Data

Aug. 18, 1999 (JP) ............................................. 11-231788
Jul. 13, 2000 (JP) ........................................ 2000-212927

(51) Int. Cl.$^7$ ............................................... A61F 13/15
(52) U.S. Cl. ............. 604/396; 604/385.11; 604/385.01
(58) Field of Search ........................... 604/396, 385.01, 604/387, 382, 385.11

(56) References Cited

U.S. PATENT DOCUMENTS

| | | |
|---|---|---|
| 4,610,681 A | 9/1986 | Strohbeen et al. |
| 5,163,932 A * | 11/1992 | Nomura et al. ........... 604/385.2 |
| 5,236,430 A * | 8/1993 | Bridges ....................... 604/396 |
| 5,628,738 A * | 5/1997 | Suekane .................. 604/385.1 |
| 5,746,731 A * | 5/1998 | Hisada ..................... 604/385.2 |
| 5,817,087 A | 10/1998 | Takabayashi et al. |
| 5,931,827 A * | 8/1999 | Buell et al. ............... 604/385.2 |

FOREIGN PATENT DOCUMENTS

| | | |
|---|---|---|
| EP | 0295957 | 12/1988 |
| GB | 2257652 | 1/1993 |
| JP | 9287 | 5/1997 |
| TW | 286277 | 9/1996 |
| WO | 9500096 | 1/1995 |

* cited by examiner

Primary Examiner—John G. Weiss
Assistant Examiner—Jacqueline F Stephens
(74) Attorney, Agent, or Firm—Birch, Stewart, Kolasch & Birch, LLP

(57) ABSTRACT

A shorts type absorbent article comprising a liquid-permeable topsheet 2, a liquid-impermeable antileakage sheet and a liquid-retentive absorbent core 4, opposing left and right side edge portions of a stomach-side zone A and opposing left and right side edge portions of a back-side zone B being joined together to thereby form one pair of joined-sections 9, wherein the joined sections 9 include securely joined sections which are joined by being pressed substantially from both a surface on the side of the stomach-side zone A and a surface on the side of the back-side zone B, moderately joined sections which are joined by being pressed substantially from either the surface on the side of the stomach-side zone A or the surface on the side of the back-side zone B and non-joined sections which are not substantially pressed from either the surface on the side of the stomach-side zone A or the surface on the side of the back-side zone B, the joined sections having three or more stages of thickness in section.

4 Claims, 5 Drawing Sheets

ABSORBENT ARTICLE

BACKGROUND OF THE INVENTION

1. Field of the Invention

This invention relates to a shorts type absorbent article such as a shorts type disposable diaper and a shorts type sanitary napkin having a joined section which is excellent in strength, feel and peelability.

2. Description of the Related Art

Heretofore, a wide variety of shorts type absorbent articles have been proposed, which includes a liquid-permeable topsheet, a liquid-impermeable antileakage sheet and a liquid-retentive absorbent core, and in which opposing left and right side edge portions of a stomach-side portion and opposing left and right side edge portions of a back-side portion are joined together to thereby form a pair of joined sections.

However, in the conventional shorts type absorbent articles, the joined section is formed in such a manner that it is sandwiched and pressed between a joining block having an even surface and another joining block having concavity and convexity configurations. Thus, the joined section comprises first regions which are pressed from the both surfaces and second regions which are pressed from only one surface thereof. In the conventional absorbent articles having such a joined section, since the joined section is stiff, it irritates the wearer's skin and the feel is not good enough.

There have also been contemplated those in which the joined section comprises first regions which are joined by being pressed from both surfaces and second regions which are not pressed from either surface. Absorbent articles having such a joined section are greatly reduced in stiffness but only at the sacrifice of the joining strength. Moreover, those absorbent articles have such an inconvenience that the regions (first regions), which are pressed from both surfaces, are extremely reduced due to swaying on an actual machining tool and a desired joining strength is unobtainable.

Furthermore, such a shorts type disposable diaper as disclosed in Japanese Utility Model Laid-Open Publication (Kokai) No. Hei 9-287 is known. In this disposable diaper, a nonwoven fabric containing thermoplastic fibers is thermally bonded to opposite side edge portions of the shorts by varying the joining width such that a joined section having difference in joining strength is arranged adjacent to the vertical direction of the shorts.

However, in the absorbent article of this technique, since the joined section, which is varied in joining width so as to have difference in joining strength, is arranged adjacent to the vertical direction of the shorts, the feel is bad. Moreover, since the joining strength is of two stages, peelability is not good. Furthermore, there is a fear that discharged wastes leak through a gap between the adjacent joined sections.

SUMMARY OF THE INVENTION

It is, therefore, an object of the present invention to provide a shorts type absorbent article which is provided with a joined section having sufficient strength, excellent feel and texture and superior peelability.

From one aspect of the present invention, the above object has been achieved by providing a shorts type absorbent article comprising a liquid-permeable topsheet, a liquid-impermeable antileakage sheet and a liquid-retentive absorbent core, opposing left and right side edge portions of a stomach-side zone and opposing left and right side edge portions of a back-side zone being joined together to thereby form one pair of joined-sections, wherein the joined sections include securely joined sections which are joined by being pressed substantially from both a surface on the side of the stomach-side zone and a surface on the side of the back-side zone, moderately joined sections which are joined by being pressed substantially from either the surface on the side of the stomach-side zone or the surface on the side of the back-side zone and non-joined sections which are not substantially pressed from either the surface on the side of the stomach-side zone or the surface on the side of the back-side zone, the joined sections having three or more stages of thickness in section.

From another aspect of the present invention, the above object has been achieved by providing a method for manufacturing the above-mentioned absorbent article, comprising a joining step for forming one pair of left and right joined sections by pressing one pair of joining blocks having predetermined concavity and convexity configurations from both the surface on the side of the stomach-side zone and the surface on the side of the back-side zone, the one pair of joining blocks used in the joining step, having the concavity and convexity configuration formed by arranging a plurality of convexities linearly at predetermined intervals, a cross angle $\alpha$ formed between straight lines formed by the convexities of one of the joining blocks and straight lines formed by said convexities of the other side of the joining block being set to 0 degree<$\alpha$<180 degree, or otherwise the one pair of joining blocks, having the concavity and convexity configuration formed by arranging a plurality of convexities linearly at predetermined intervals, a cross angle $\alpha$ between straight lines formed by the convexities of one of the joining blocks and straight lines formed by the convexities of the other of the joining blocks being set to $\alpha$=0 or $\alpha$=180 degree, and a ratio between a width of each convexity of the one joining block and a width of each convexity of the other joining block being set to 1.3 or more.

The absorbent article of the present invention has sufficient strength, excellent feel and peelability in its joined sections.

DETAILED DESCRIPTION OF THE INVENTION

Figure 1:
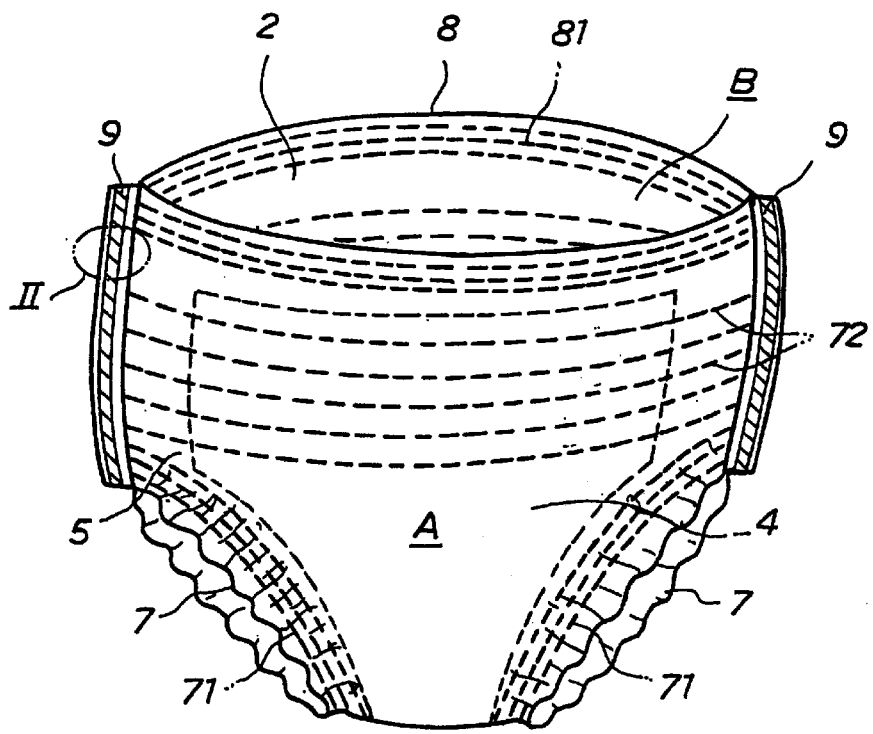
FIG. 1 is a perspective view showing a disposable diaper as a first embodiment of an absorbent article of the present invention.
Figure 2:
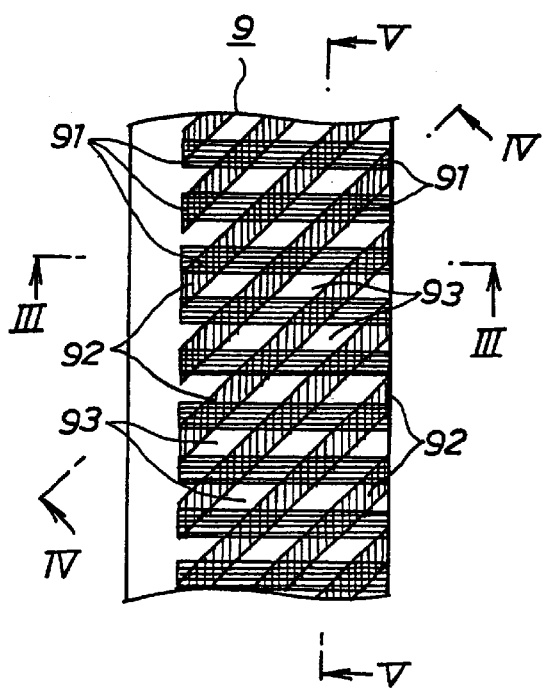
FIG. 2 is an enlarged view of that portion which is indicated by II of FIG. 1.
Figure 3:
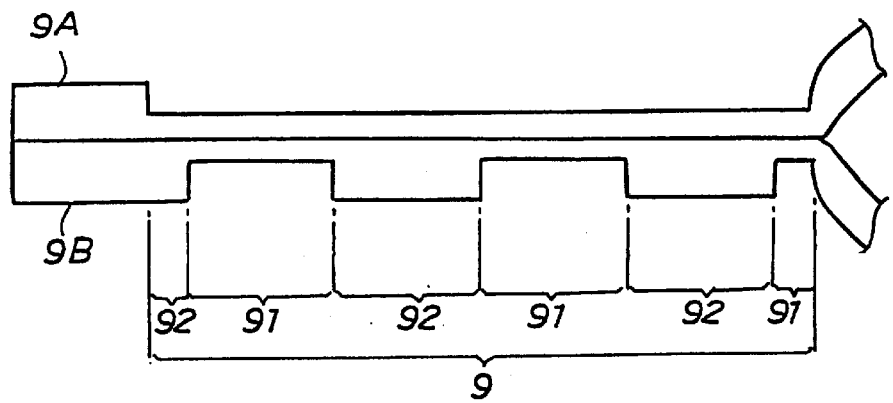
FIG. 3 is a sectional view taken on line III—III of FIG. 2.
Figure 4:
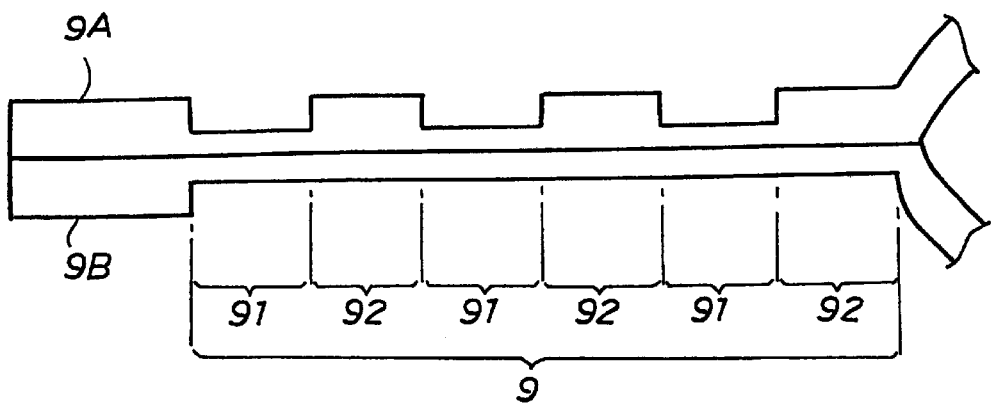
FIG. 4 is a sectional view taken on line IV—IV of FIG. 2.
Figure 5:
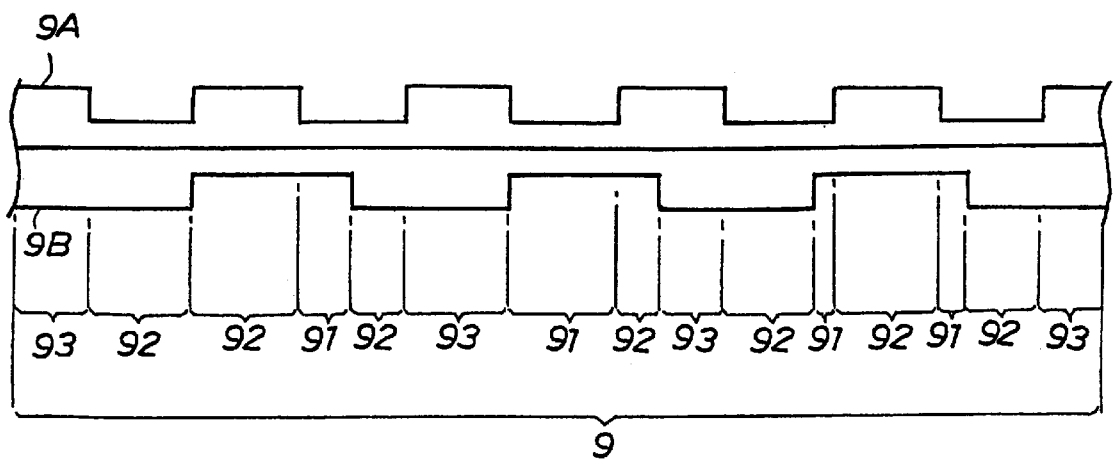
FIG. 5 is a sectional view taken on line V—V of FIG. 2.

An absorbent article and a method of manufacturing the same according to the present invention will now be described in the form of one preferred embodiment.

A shorts type disposable diaper 1 as a first embodiment of an absorbent article of the present invention comprises a liquid-permeable topsheet 2, a liquid-impermeable antileakage sheet (not shown) and a liquid-retentive absorbent core 4. Left and right side edge portions of a stomach-side zone A and left and right side edge portions of a back-side zone B are joined together, respectively, to thereby form one pair of joined sections 9.

In the disposable diaper 1 of this embodiment, the absorbent core 4 has the narrower middle area, thus exhibiting an hourglass-like configuration. Both the topsheet 2 and the antileakage sheet exhibit a similar configuration in match with an external configuration of the absorbent core 4. The topsheet 2 and the antileakage sheet are also joined together, not shown in particular though, at those areas located outward of longitudinal side edges of the absorbent core 4. They are also extended from longitudinal end edges of the absorbent core 4 and adhered together.

Two outer layer nonwoven fabrics 5 are disposed at a reverse side of the antileakage sheet. The outer layer nonwoven fabrics 5 are extended towards more outer side of the disposable diaper than side edges of the absorbent core 4. Side flaps 7 and a waist opening portion 8 are formed by such extended outer layer nonwoven fabrics 5. Waist opening elastic members 81, leg opening elastic members 71 and waist elastic members 72 are arranged between those two outer layer nonwoven fabrics 5, 5, thereby forming waist opening portion gathers, leg opening portion gathers and waist portion gathers, respectively. This construction is the same as the common shorts type disposable diapers.

In the shorts type disposable diaper 1 of this embodiment, the joined section 9 includes, as shown in FIGS. 2 to 5, a number of securely joined sections 91 which are joined by being pressed substantially from both sides, namely from a surface 9A on the side of the stomach-side zone A and a surface 9B on the side of the back-side zone B, a number of moderately joined sections 92 which are joined by being pressed substantially from either one of the sides, namely, from either the surface 9A on the side of the stomach-side zone A or the surface 9B on the side of the back-side zone B and a number of non-joined sections 93 which are pressed from neither the surface 9A on the side of the stomach-side zone A nor the surface 9B on the side of the back-side zone B. The joined section 9 has substantially three stages of thickness in section.

More specifically, in this embodiment, the joined section 9 is linearly pressed along the orthogonal direction to the longitudinal direction of the joined section 9 from the surface 9A on the side of the stomach-side zone A, and it is linearly pressed along the oblique direction to the longitudinal direction of the joined section 9 from the surface 9B on the side of the back-side zone B. Consequently, the securely joined sections 91 are formed by those areas where orthogonal linear lines and the oblique linear lines are overlapped, the moderately joined sections 92 are formed by those areas where either one of the two linear lines is present, and the non-joined sections 93 are formed by those areas where none of the two linear lines are present.

The securely joined sections 91, the moderately joined sections 92 and the non-joined sections 93 are all formed in a parallelogram. Moreover, those three kinds of sections 91, 92, 93 are arranged such that they are present alternately.

The above expression "substantially three stages of thickness" refers to that three stages of thickness are formed by three kinds of the joined sections 91, 92, 93. Specifically, the securely joined sections 91, which are pressed from both of the surfaces 9A, 9B, are mostly reduced in thickness, the moderately joined sections 92, which are pressed from one of the surfaces 9A and 9B, are intermediately reduced in thickness, and the non-joined sections 93, which are pressed from neither the surface 9A nor surface 9B, is least reduced in thickness (i.e., largest in thickness).

The total area of the moderately joined sections 92 are preferably 10 to 60% of the total area of the joined section 9. Moreover, it is preferred that the moderately joined sections 92 each having an area of 0.5 to 10 mm$^2$ are disposed in number of 5 to 25 pc/cm$^2$. Moreover, they are preferably disposed over the almost entire area of the joined section 9 as in this embodiment.

The ratio of the securely joined sections and the non-joined sections can be properly selected. However, the ratio is preferably 5/95 to 95/5. If the ratio of the total area of the moderately joined sections 92 is set to 10% or more, peel-off can be made smoothly. In contrast, if the ratio is set to 60% or less, the feel of either the surface 9A or surface 9B of the joined section 9 becomes good. If the area of the moderately joined sections 92 is set to 0.5 mm$^2$ or more, peel-off can be made smoothly. In contrast, if the area is set to 10 mm$^2$ or less, the feel of either the surface 9A or surface 9B of the joined section 9 becomes good. Moreover, if the density is set to 5 pc/cm$^2$ or more, peel-off can be made smoothly. In contrast, if the density is set to 25 pc/cm$^2$ or less, the feel of either the surface 9A or surface 9B of the joined section 9 becomes good. The width of the joined section 9 is preferably set to 4 to 10 mm.

The joining strength of the securely joined sections 91 is preferably set to 1000 to 4000 cN/30 mm. The joining strength of the moderately joined sections 92 is preferably set to 300 to 2000 cN/30 mm. The joining strength of the joined section 9 as a whole is preferably set to 1000 to 4000 cN/30 mm. Here, the joining strength can be measured in the following manner. The respective sections are cut out each having an appropriate dimension and used as samples. A 180 degree peel strength of the samples thus obtained is measured at a peel rate of 300 mm/min by a tensile strength tester and the measured value is converted to a width of 30 mm. With respect to the securely joined sections 91 and the moderately joined sections 92, the peel strength may be measured using those samples having a large width which are simulatively produced under the same conditions as the respective sections.

The material for forming the respective component members of the disposable diaper of this embodiment may be selected from those generally known without any particular limitation.

The disposable diaper of this embodiment thus constructed can be used in the same manner as the common shorts type disposable diapers. Since the disposable diaper 1 of this embodiment has the joined section 9 comprising the securely joined sections 91, the moderately joined sections 92 and the non-joined sections 93, it has a joining strength enough not to be detached in wear. Moreover, it is excellent in feel and less irritating to the wearer's skin. Furthermore, since there are three stages of thickness, feel to the skin is smooth. Moreover, since there are three stages of joining strength, peeling-off of the joined section, which is usually done when the diaper is taken off and wrapped, is smoothly made according to the disposable diaper of this embodiment. In addition, since the securely joined sections and the moderately joined sections are formed continuously, the leakage of discharged wastes can reliably be prevented.

Figure 6:
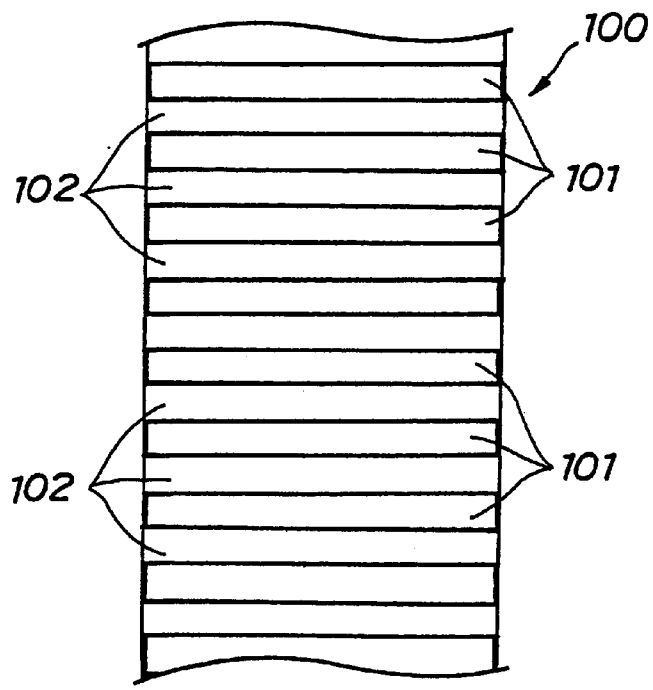
FIG. 6 is a partly enlarged view showing one embodiment of a joining block.
Figure 7:
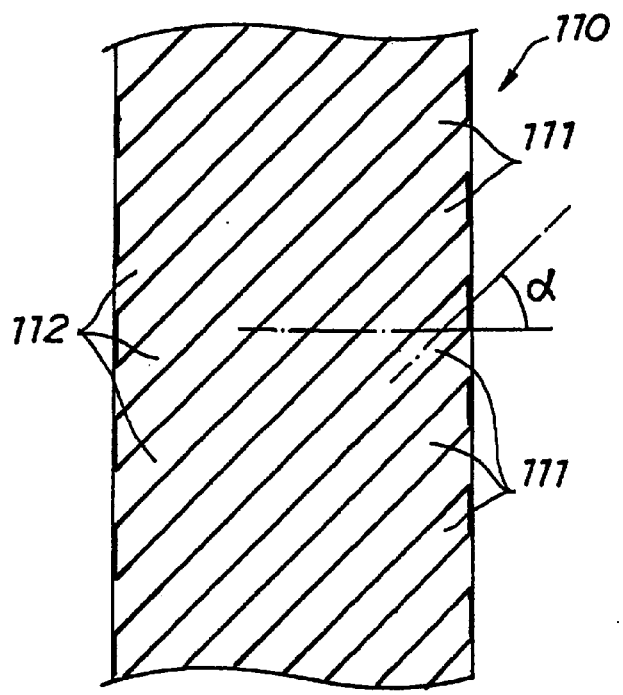
FIG. 7 is a partly enlarged view showing another embodiment of the joining block.
Figure 8:
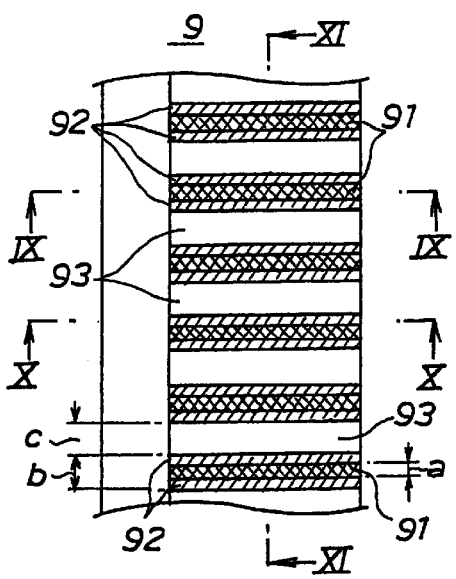
FIG. 8 is a partly enlarged view (corresponding to FIG. 2) of a joined section in another embodiment of an absorbent article of the present invention.
Figure 9:
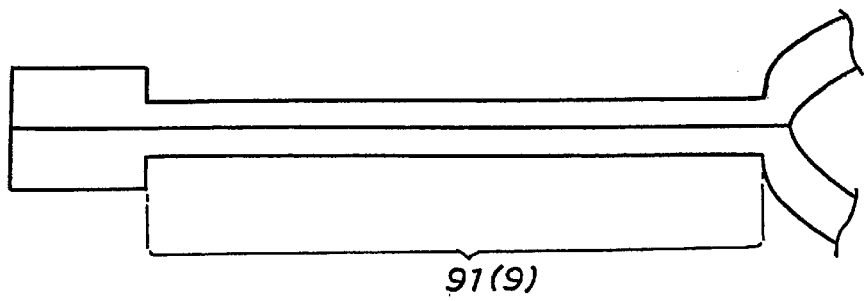
FIG. 9 is a sectional view taken on line IX—IX of FIG. 8.
Figure 10:
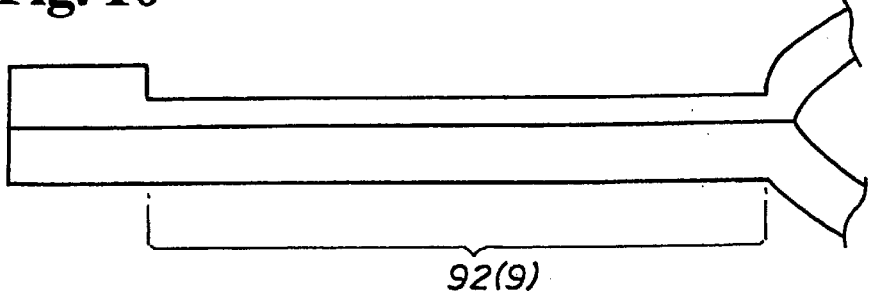
FIG. 10 is a sectional view taken on line X—X of FIG. 8.
Figure 11:
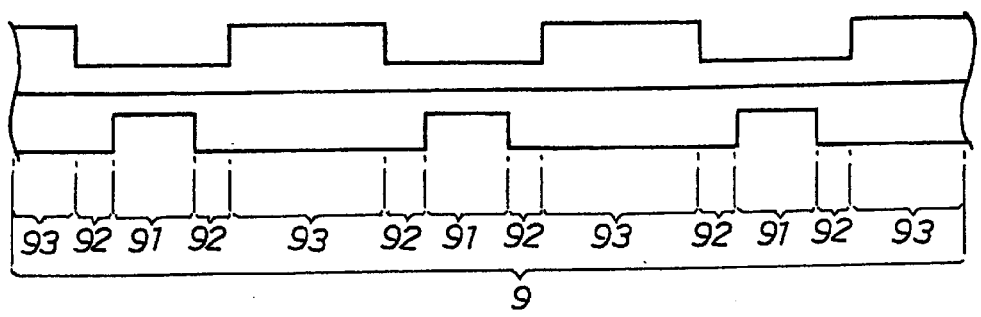
FIG. 11 is a sectional view taken on line XI—XI of FIG. 8.

Next, a method for manufacturing the above-mentioned absorbent article of the present invention will be described in the form of one preferred embodiment. A method for manufacturing a disposable diaper of this embodiment can be carried out by executing a joining step for pressing a pair of joining blocks 100, 110 (see FIGS. 6 and 7) having predetermined convexities and concavities from both surfaces, one on the side of the stomach-side zone and the other on the side of the back-side zone, to thereby form a pair of left and right joined sections. At that time, as the one pair of joining blocks 100, 110 used in the joining step, as shown in FIGS. 6 and 7, there can be used those blocks 100, 110 which are different in configuration of the convexities and concavities, and in both of which the convexities 101, 111 are linearly arranged at predetermined intervals, and a cross angle α between the straight lines formed by the convexities 101 of the first joining block 100 and the straight lines formed by the convexities 111 of the second joining block 110 (see FIG. 7) is set to 0 degree<α<180 degree and preferably 45 degree<α<70 degree or 110 degree<α<135 degree.

More specifically, the size dimension of the joining blocks 100, 110 is optional in accordance with the size dimension of the joined section(s) to be formed. Moreover, the size dimension and the interval (i.e., width of the concavities 102, 112) of the convexities are optional in accordance with the securely joined sections, the moderately joined sections and the non-joined sections. Furthermore, the convexities 101 of the joining block 100 are formed along the orthogonal direction to the longitudinal direction of the joining block 100, while the convexities 111 of the joining block 110 are formed along the oblique direction to the longitudinal direction of the joining block 110. Moreover, the pressing operation can be carried out in the same manner as in the common embossing operation, only except that the joining blocks 100, 110 are used. Furthermore, all the other steps, for example, the adhering step of various members, than the joining step can be carried out in the same manner as in the method for manufacturing the common disposable diapers.

Next, an absorbent article according to a second embodiment will be described. It should be noted that in the description to follow, only those points, which are different from the first embodiment, are described. Those points, which are not specifically described, the description made with respect to the first embodiment is applicable, where appropriate. A disposable diaper 1 as an absorbent article of the second embodiment includes securely joined sections 91, moderately joined sections 92 and non-joined sections 93 which are all linearly formed along the orthogonal direction to the longitudinal direction of the joined section 9 as shown in FIGS. 8 to 11. The securely joined sections 91 and the non-joined sections 93 are each sandwiched between the adjacent moderately joined sections 92.

More specifically, the width a of each securely joined section 91 is preferably 0.5 to 1.5 mm, the width b between the outermost edges of the moderately joined sections 92, 92 which are present in such a manner as to sandwichingly holding the securely joined section 91 is preferably 0.5 to 1.5 mm, and the width c of each non-joined section 93 is preferably 0.5 to 1.5 mm. The ratio b/a between the width a and the width b is preferably 1.3 or more and more preferably 1.4 to 1.6. If the ratio is set to 1.3 or more, sufficient joining strength can be obtained which would otherwise be unobtainable because the number of the securely joined sections is reduced due to swaying at the time of manufacture. Moreover, the area of the moderately joined sections becomes constant and thus, smooth peel-off can be made. The disposable diaper of this embodiment exhibits the same effect as the disposable diaper of the first embodiment.

Next, a method for manufacturing the above-mentioned absorbent article will be described in the form of one preferred embodiment of the present invention. In the description to follow, only those points, which are different from the method for manufacturing the disposable diaper of the first embodiment, are described. Those points, which are not specifically described, the description made with respect to the method for manufacturing the disposable diaper of the first embodiment is applicable, where appropriate.

Figure 12:
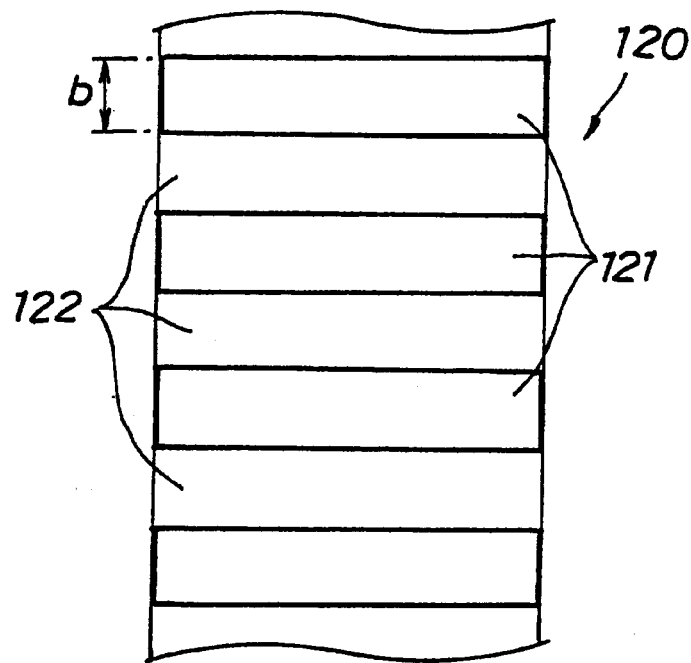
FIG. 12 is a partly enlarged view showing another embodiment of the joining block.
Figure 13:
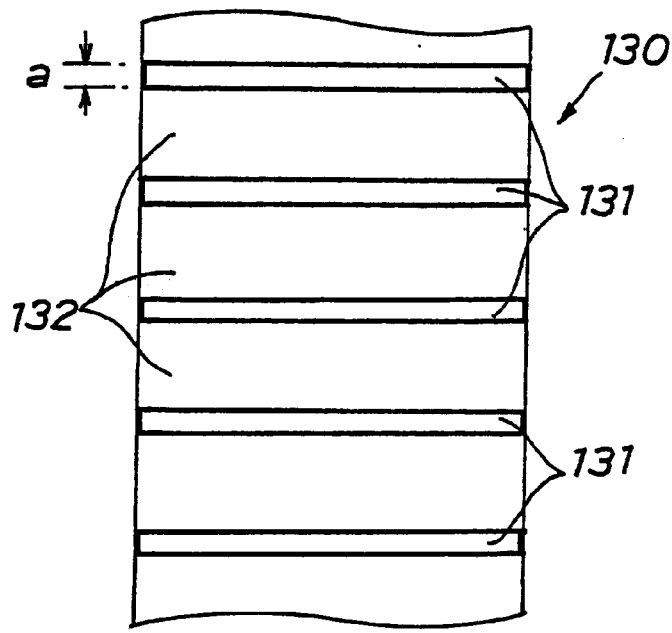
FIG. 13 is a partly enlarged view showing still another embodiment of the joining block.

A method for manufacturing an absorbent article of this embodiment can be carried out by executing a joining step for pressing a pair of joining blocks 120, 130 (see FIGS. 12 and 13) having predetermined convexities and concavities from both surfaces, the one on the side of the stomach-side zone and the other on the side of the back-side zone to thereby form a pair of left and right joined sections. At that time, as the one pair of joining blocks 120, 130 used in the joining step, as shown in FIGS. 12 and 13, there can be used those blocks 120, 130 which are different in configuration of the convexities and concavities, and in both of which the convexities 121, 131 are linearly arranged at predetermined intervals, and a cross angle α between the straight lines formed by the convexities 121 of the first joining block 120 and the straight lines formed by the convexities 131 of the second joining block 130 is set to α=0 or α=180 degree and the ratio b/a between the width b of each convexity 121 of the first joining block 120 and the width a of each convexity 131 of the second joining block 130 is set to 1.3 or more, and preferably 1.4 to 1.6.

Moreover, the convexities 121 of the joining block 120 and the convexities 131 of the joining block 130 are formed along the orthogonal direction to the longitudinal direction of the joining blocks 120, 130, respectively. All the other points than the above, can be carried out in the same manner as in the manufacturing method of the first embodiment.

It should be noted that the present invention can be changed in many ways without being limited to the above-mentioned first and second embodiments. Although it is preferred for the present invention that the sectional thickness of the joined section is of three stages and the joining strength is of three stages, it is also accepted that the sectional thickness of the joined section is of four or more stages and the joining strength is of four or more stages. Moreover, in the above embodiments, although a disposable diaper is exemplified for description, the present invention can likewise be applied to a sanitary napkin, an incontinent pad and the like.

[Embodiment 1]

A disposable diaper of the above-mentioned first embodiment was manufactured, in which the width of each linear convexity orthogonally directed to the longitudinal direction of a joining block shown in FIG. 6 is 0.7 mm, the width of each linear convexity obliquely directed to a joining block shown in FIG. 7 is 2.5 mm, the area dimension of each securely joined section is 1.75 mm$^2$ and the density is 16.7 pc/cm$^2$, the area dimension of each moderately joined section is 3.05 mm$^2$ and the density is 16.7 pc/cm$^2$, and the area dimension of each non-joined section is 1.2 mm$^2$ and the density is 16.7 pc/cm$^2$.

[Embodiment 2]

A disposable diaper of the above-mentioned second embodiment was manufactured, in which the width of each linear convexity orthogonally directed to the longitudinal direction of a joining block shown in FIG. 12 is 1 mm, the width of each linear convexity orthogonally directed to the longitudinal direction of a joining block shown in FIG. 13 is 0.7 mm, the area dimension of each securely joined section is 5.6 mm$^2$ and the density is 8.3 pc/cm$^2$, the area dimension of each moderately joined section is 2.4 mm$^2$ and the density is 8.3 pc/cm$^2$, and the area dimension of each non-joined section is 4.0 mm$^2$ and the density is 8.3 pc/cm$^2$.

[Embodiment 3]

A disposable diaper of the above-mentioned first embodiment was manufactured, in which the width of each linear convexity orthogonally directed to the longitudinal direction of a joining block shown in FIG. 6 is 0.7 mm, the width of each linear convexity obliquely directed to a joining block shown in FIG. 7 is 1.5 mm, the area dimension of each securely joined section is 1.05 mm$^2$ and the density is 22.2 pc/cm$^2$, the area dimension of each moderately joined section is 2.25 mm$^2$ and the density is 22.2 pc/cm$^2$, and the area dimension of each non-joined section is 1.2 mm$^2$ and the density is 22.2 pc/cm$^2$.

[Embodiment 4]

A disposable diaper of the above-mentioned first embodiment was manufactured, in which the width of each linear convexity orthogonally directed to the longitudinal direction of a joining block shown in FIG. 6 is 0.7 mm, the width of each linear convexity obliquely directed to a joining block shown in FIG. 7 is 3.0 mm, the area dimension of each securely joined section is 2.1 mm$^2$ and the density is 16.7 pc/cm$^2$, the area dimension of each moderately joined section is 3.1 mm$^2$ and the density is 16.7 pc/cm$^2$, and the area dimension of each non-joined section is 0.8 mm$^2$ and the density is 16.7 pc/cm$^2$.

[Embodiment 5]

A disposable diaper of the above-mentioned second embodiment was manufactured, in which the width of each linear convexity orthogonally directed to the longitudinal direction of a joining block shown in FIG. 12 is 1.72 mm, the width of each linear convexity orthogonally directed to the longitudinal direction of a joining block shown in FIG. 13 is 2 mm, the area dimension of each securely joined section is 13.8 mm$^2$ and the density is 4.2 pc/cm$^2$, the area dimension of each moderately joined section is 2.2 mm$^2$ and the density is 4.2 pc/cm$^2$, and the area dimension of each non-joined section is 8.0 mm$^2$ and the density is 4.2 pc/cm$^2$.

[Embodiment 6]

A disposable diaper of the above-mentioned first embodiment was manufactured, in which the width of each linear convexity orthogonally directed to the longitudinal direction of a joining block shown in FIG. 6 is 0.5 mm, the width of each linear convexity obliquely directed to the longitudinal direction of a joining block shown in FIG. 7 is 3.3 mm, the area dimension of each securely joined section is 1.65 mm$^2$ and the density is 16.7 pc/cm$^2$, the area dimension of each moderately joined section is 3.65 mm$^2$ and the density is 16.7 pc/cm$^2$, and the area dimension of each non-joined section is 0.7 mm$^2$ and the density is 16.7 pc/cm$^2$.

COMPARATIVE EXAMPLES 1 to 3

A joined section was formed by pressing the entire surfaces on the both surface sides (Comparative Example 1). A joined section which was formed by pressing one surface over its entire surface and the other surface by using the joining block shown in FIG. 6 (Comparative Example 2). A joined section was formed by using the same joining block on the both surfaces (Comparative Example 3). By doing so, disposable diapers were obtained respectively.

That is, the disposable diaper of Comparative Example 1 has neither moderately joined sections nor non-joined sections, the disposable diaper of Comparative Example 2 has no non-joined sections, and the disposable diaper of Comparative Example 3 has no moderately joined sections.

Test Example

The obtained disposable diapers were evaluated in strength, feel and texture, peelability and from an aspect of equipment. The result is shown in Table 1.

Strength (method of evaluation): A joined section joined under the conditions of same temperature, same pressure and same period of time is cut into a width of 30 mm and a 180 degree peel strength of the same is measured at a peel rate of 300 mm/min by a tensile strength tester.

⊚: more than 4000 cN/30 mm

○: 1000 to 4000 cN/30 mm

Δ: 500 to 1000 cN/30 mm

X: less than 500 cN/30 mm

Feel and Texture (method of evaluation): An organoleptic evaluation by hand touch. The joined section is felt by finger.

⊚: very soft

○: soft

Δ: rather stiff and rough

X : stiff and irritating

Peel-off (method of evaluation): The joined section is actually peeled off by hand to see how the force is applied and how the peeled-off area is torn.

⊚: easily peelable.

○: peelable without applying large force and with no tear of the material.

Δ: Large force is required for peeling off and tear of the material sometimes occurs.

X: Very large force is required for peeling off and the material is torn.

Aspect of Equipment

○: The joining block is easy in positional adjustment and stable production is possible.

Δ: Adjustment is difficult but stable production is possible.

X: Adjustment is difficult, and strength and the like are unstable during production.

TABLE 1

|  |  | Area Ratio (%) | | | | | | |
| --- | --- | --- | --- | --- | --- | --- | --- | --- |
|  |  | Securely Joined Sections | Moderately Joined Sections | Non-joined Section | Strength | Feel | Peelability | Aspect of Equipment |
| Example | 1 | 29.2 | 50.8 | 20.0 | ○ | ○ | ◎ | ○ |
|  | 2 | 46.7 | 20.0 | 33.3 | ○ | ○ | ◎ | ○ |
|  | 3 | 23.3 | 50.0 | 26.7 | ○ | ○ | ○ | ○ |
|  | 4 | 35.0 | 51.7 | 13.3 | ○ | ○ | ○ | ○ |
|  | 5 | 57.5 | 9.2 | 33.3 | ○ | ○ | △ | ○ |
|  | 6 | 27.5 | 60.8 | 11.7 | △ | ○ | ◎ | ○ |
| Comparative Example | 1 | 100 | 0 | 0 | ◎ | x | x | ○ |
|  | 2 | 46.7 | 53.3 | 0 | ○ | △ | △ | ○ |
|  | 3 | 46.7 | 0 | 53.3 | A | ◎ | ○ | x |

What is claimed is:

1. A shorts type absorbent article comprising a liquid-permeable topsheet, a liquid-impermeable antileakage sheet and a liquid-retentive absorbent core, opposing left and right side edge portions of a stomach-side zone and opposing left and right side edge portions of a back-side zone being joined together to thereby form one pair of joined-sections, wherein said joined sections include securely joined sections which are joined by being pressed substantially from both a surface on a side of said stomach-side zone and a surface on a side of said back-side zone, moderately joined sections which are joined by being pressed substantially from either the surface on the side of said stomach-side zone or the surface on the side of said back-side zone and non-joined sections which are not substantially pressed from either the surface on the side of said stomach-side zone or the surface on the side of said back-side zone, said joined sections having three or more stages of thickness in section.

2. The absorbent article according to claim 1, wherein a total area of said moderately joined sections are 10 to 60% of a total area of said joined section, and said moderately joined sections each having an area of 0.5 to 10 mm² are disposed in number of 5 to 25 pc/cm² over almost the entire area of said joined section.

3. A method for manufacturing the absorbent article as defined in claim 1, comprising:

a joining step for forming one pair of left and right joined sections by pressing one pair of joining blocks having predetermined concavity and convexity configurations from both the surface on the side of said stomach-side zone and the surface on the side of said back-side zone, said one pair of joining blocks used in said joining step, having the concavity and convexity configuration formed by arranging a plurality of convexities linearly at predetermined intervals, a cross angle α between straight lines formed by said convexities of one of said joining blocks and straight lines formed by said convexities of the other of said joining blocks being set to 0 degree<α<180 degree.

4. A method for manufacturing the absorbent article as defined in claim 1, comprising:

a joining step for forming a pair of left and right joined sections by pressing one pair of joining blocks having predetermined concavity and convexity configurations from both the surface on the side of said stomach-side zone and the surface on the side of said back-side zone, said one pair of joining blocks used in said joining step, having the concavity and convexity configuration formed by arranging a plurality of convexities linearly at predetermined intervals, a cross angle α between straight lines formed by said convexities of one of said joining blocks and straight lines formed by said convexities of the other of said joining blocks being set to α=0 or α=180 degree, and a ratio between a width of each convexity of said one joining block and a width of each convexity of said other joining block being set to 1.3 or more.

* * * * *